United States Patent [19]
Anton et al.

[11] Patent Number: 5,547,844
[45] Date of Patent: Aug. 20, 1996

[54] HELICOBACTER PYLORI BACTERIAL DERIVED FACTOR

[75] Inventors: Peter A. Anton, West Hollywood; Joseph R. Reeve, Jr., Oakhurst; John H. Walsh; Kym F. Faull, both of Los Angeles, all of Calif.

[73] Assignee: The Regents of the University of California, Oakland, Calif.

[21] Appl. No.: 395,495

[22] Filed: Feb. 23, 1995

[51] Int. Cl.$^6$ .............................. G01N 33/53; C12N 1/00
[52] U.S. Cl. ............................................ 435/7.1; 435/7.71
[58] Field of Search ................................. 435/7.1, 7.71, 435/243

[56] References Cited

U.S. PATENT DOCUMENTS 5,385,739  1/1995  Debregeas et al. ..................... 424/494

OTHER PUBLICATIONS

Reymunde, et al., Production Of Chemoattractant by *Helicobacter pylori* (Sep. 1993) Digestive Diseases And Sciences, vol. 38, No. 9, pp. 1697–1701.
Crabtree, et al., Interleukin–8 Expression in *Helicobacter pylori* Infected, Normal, And Neoplastic Gastroduodenal Mucosa (1994) J. Clin. Pathol.; 47:61–66.
"Kozol, et al., A Neutrophil Chemotactic Factor Present In *H. pylori* But Absent In H. Mustelae" (Jan. 1993) Digestive Diseases & Sciences, vol. 38, No. 1, pp. 137–141.
J. L. Wallace, Possible Mechanisms and Mediators of Gastritis Associated with *Helicobacter pylori* Infection (Undated) University of Calgary, Calgary, Alberta, Canada.

Norgaard, et al., Activation of Human Phagocytes By *Helicobacter pylori*. A Noval Interaction With Neutrophils and Monocytes Distinct From That of N–Formylated Oligopeptides (1993) Zbl. Bakt. 280, 86–92.
Mai, et al., Surface Proteins From *Helicobacter pylori* Exhibit Chemotatic Activity For Human Leukocytes and Are Presentin Gastric Mucosa (Feb. 1992) The Journal of Experimental Medicine, vol. 175, pp. 517–525.
Craig, et al., *Helicobacter pylori* Secretes A Chemotactic Factor For Monocytes And Neutrophils (Nov. 1991) UCLA School of Medicine, Los Angeles, California.
Driven, et al., Determination of Four Metabilites Of The Plasticizer D192—Ethylhexylo Phthalate In Human Urine Samples (1993) Int. Arch Occup Environ Health 64:555–560.
Nielse, et al., Chemotactic Activity of *Helicobacter pylori* Sonicate For Human Polymorphonuclear Leucocytes and Monocytes (1992) Gut, 33:738–742.

*Primary Examiner*—James C. Housel
*Assistant Examiner*—Ginny Allen Portner
*Attorney, Agent, or Firm*—Bertram I. Rowland

[57] ABSTRACT

Chemotactin, diethyl phthalate, is shown to be a chemoattractant secreted by *H. pylori*. Chemotactin attracts phagocytic cells with a resulting inflammatory episode. Chemotactin and its metabolites may be used for diagnosis and monitoring courses of infection by *H. pylori* or other chemotactin secreting organisms. In addition, chemotactin may be used in research for studying the inflammatory process, for identifying new drugs for modulating chemoattraction and activation of phagocytic cells, and for inducing an inflammatory response as a therapeutic intervention.

7 Claims, No Drawings

HELICOBACTER PYLORI BACTERIAL DERIVED FACTOR

This invention was made in the course of research supported by a grant from NIH. The U.S. government may have rights in any claims of a patent issuing on this application.

INTRODUCTION

1. Technical Field

The field of this invention is inflammatory response.

2. Background

The inflammatory response is an essential part of the protective mechanisms associated with pathogens. The inflammatory process involves the secretion of a wide number of factors which serve to activate various cells capable of lytic activity toward foreign cells, as well as non-selective agents which are cytotoxic. Included among these agents are singlet oxygen, peroxides, proteases, and the like. These non-specific agents not only attack an invading pathogen, but can also attack native tissue.

As part of the inflammatory process, chemoattractants are produced, to attract those hematopoietic cells involved with protection of the host. In this way, the body's defense systems may be mobilized rapidly to a site of infection.

*Helicobacter pylori* is strongly associated with superficial antral gastritis. While *H. pylori* is believed to be the causal agent of this inflammation, bacteria are rarely seen in the setting of histologically normal antral mucous. A strong correlation has been observed between the severity of the inflammation and the number of bacteria seen on the gastric luminal side of the mucosa. It has therefore been postulated that the *H. pylori* secretes a factor that attracts leukocytes causing the inflammatory response. Many bacteria have been shown to secrete such factors, often characterized as low molecular weight, amino-formylated peptides.

In order to develop therapies, diminish the inflammatory response and better understand the mechanism of chemoattractants, particularly the chemoattractant associated with *H. pylori*, it is of great interest to be able to identify the agents involved in the inflammatory process associated with *H. pylori* infection.

RELEVANT LITERATURE

Craig et al. Gut (1992) 33:1020-3 reports that *H. pylori* secretes a chemotactic factor for monocytes and neutrophils. See also Reymunde et al. Digestive Diseases and Sciences (1993) 38:1697–701. Secretion of IL-8 by *H. pylori* is reported by Crabtree et al. J. Clinical Pathology (1994) 47:61–6. The presence of a chemotactic factor in *H. pylori* but not *H. mustelae* is reported by Kozol et al. Digestive Diseases and Sciences (1993) 38:137–41. A review of *H. pylori* infection and its relationship to gastritis is described by Wallace, Scandinavian Journal of Gastroenterology. Supplement (1991) 187:65–70. Norgaard et al. International Journal of Medical Microbiology, Virology, Parasitology and Infectious Diseases (1993) 280:86–92 reports the activation of human phagocytes by *H. pylori*. Nielsen and Andersen report a chemotactic activity in *H. pylori* sonicate. See also Mai et al. J. Experimental Medicine (1992) 175:517–25. Elsisi et al., Fundam. Appl. Toxicol. (1989) describes the detection of diethyl phthalate in urine. See also, Scott et al., Environ. Health Perspect. (1987) 74:223–7

SUMMARY OF THE INVENTION

"Chemotactin," a chemoattractant for phagocytic cells is provided, as well as metabolic products thereof. Chemotactin results from secretion by *Helicobacter pylori* and causes an inflammatory response at the submucosa upon intestinal infection. Chemotactin and its metabolic products may be used in assays for diagnosing and monitoring *H. pylori* infection, for inducing an inflammatory response in vivo at a site of interest and in evaluating compounds for their competitive activity with chemotactin and its metabolites. Chemotactin may also be used in understanding and modulating the inflammatory process. Inhibition of chemotactin binding to its receptor can be used to modulate the inflammatory process.

DESCRIPTION OF THE SPECIFIC EMBODIMENTS

Methods and compositions are provided for identifying the presence of gastrointestinal tract tropic microorganisms which secrete chemotactin. Specifically, these methods and compositions are associated with the detection of the presence of *Helicobacter pylori* and its induction of an inflammatory response in the submucosa of the gastrointestinal tract. Chemotactin and its metabolites may be used as analytes whose detection can be related to the presence, proliferation or absence of significant infection by chemotactin secreting organisms in diagnosis and therapeutic monitoring.

Chemotactin, metabolites, and derivatives thereof may be used in assays for detecting chemotactin and its metabolites and for acting as agonists or antagonists in binding to the chemotactin cellular binding partner to induce an inflammatory response. Chemotactin can serve to act as a chemoattractant and to stimulate phagocytic cells in the induction of an inflammatory response. Inhibition of binding of chemotactin to its cellular binding partner can be used for modulating the inflammatory process to inhibit tissue damage.

Chemotactin is found to be diethyl phthalate ("DEP"), where its metabolic products may include oxidation of the ethyl groups to hydroxyethyl, oxoethyl and carboxymethyl, the monoethyl ester and the dibasic acid and its salt, particularly the physiologically acceptable salts, including sodium, potassium, ammonium, alkylated ammonium, etc.

Derivatives of chemotactin can also find use in a variety of ways, both in vitro and in vivo. The derivatives may include isotopic derivatives, where one or more of the hydrogens have been substituted with deuterium or tritium, varying from monodeuterated to perdeuterated, and from monotritiated to pertritiated. Other isotopic modifications may include the replacement of the naturally occurring carbon isotope with $^{13}C$ or $^{14}C$ and oxygen with $^{18}O$.

Various derivatives of chemotactin and its metabolites may be prepared for use in assays, as agonists or antagonists of chemotactin, for use in studying the inflammatory process, and for use as competitors with compounds being investigated for binding to the chemotactin cellular binding partner. For the most part, these compounds will have the following formula:

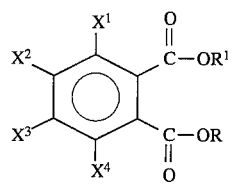

Wherein:

R and $R^1$ are hydrogen, a cation, particularly an alkali or alkaline earth metal ion, ammonium ion or proton, an alkyl group of from one to three, particularly two carbon atoms, or substituted alkyl group, having oxygen as the only heteroatom, i.e. oxy, particularly hydroxy, oxo, or carboxy, particularly the acid, where the total number of carbon atoms of each of the alkyl groups and substituents will not exceed five, usually not exceed four, wherein R and $R^1$ may be the same or different;

$X^N$ (where N indicates 1, 2, 3 and/or 4, individually or collectively) can be hydrogen, alkyl of from one to eighteen, more usually of from one to three or twelve to eighteen carbon atoms, particularly methyl, alkoxy, where the alkyl group comes within the same carbon limitations as for alkyl, non-oxo-carbonyl, including carboxy, ester and amide, where the group is of from one to twelve, usually one to six carbon atoms, halo, nitro, cyano, amino, thio, phosphorous acids, e.g. phosphate, etc. Usually, at least two of the Xs will be hydrogen, particularly $X^1$ and $X^4$. Preferably, only one of the xs will be other than hydrogen. Compounds of interest will have an affinity for the chemotactin cellular binding partner of at least about $10^{-5}M$, more preferably at least about $10^{-6}M$. The total number of carbon atoms will be not more than about thirty-six, usually not more than about thirty and is at least eight, more usually at least about ten, particularly 8 to 16. The total number of heteratoms will be at least four and not more than about twelve, more usually not more than about ten and may include oxygen, nitrogen, sulphur, phosphorous, halogen, etc.

Chemotactin and its metabolites may be used to diagnose the presence of chemotactin secreting organisms, particularly *H. pylori*, so as monitor the course of infection, e.g. to be able to detect the presence of the infection, the response of the pathogen to treatment, and the eradication of the infection, as well as the possibility of remission. By monitoring physiological sources of chemotactin and its metabolites such as urine and blood, particularly plasma, one can determine the presence or absence of such organisms, as well as the level of infection. A wide variety of assays for detecting phthalic acid and its derivatives are available. Any convenient technique may be employed, such as chromatography, e.g. gas chromatography, HPLC, TLC; immunoassays, e.g. ELISA, EMIT, FIA, etc.; mass spectrometry, and the like. The particular method will be primarily one of convenience, available equipment, desired degree of sensitivity, and the like. Depending upon the sample, the sample may be subject to varying pretreatments. For blood, the sample may be denatured by heat or other means, high molecular weight components removed by microfiltration, the analyte extracted, or the like. Urine may be processed in analogous ways, including dialysis, electrophoresis, acidification, etc. Chemotactin may be extracted from aqueous media using organic polar solvents, which may be miscible or non-miscible with water, e.g. ethanol and diethyl ether, where with miscible solvents, the diethyl phthalate may be salted out. The particular manner in which chemotactin and its metabolites are determined is not critical to this invention.

By following the level of chemotactin and/or its metabolites, one can determine the level of infection and activity of the pathogen in relation to the amount of analyte in the sample. In this way, one can rapidly detect the presence of the infection and its response to treatments, e.g. antibiotics.

As indicated above, the assays employed may be competitive or non-competitive. Where competitive assays are employed, derivatives of chemotactin and its metabolites may be employed in competition with the analyte for binding to a chemotactin binding partner, either naturally occurring, antibody, or the like. The derivatives may be labeled in a wide variety of ways allowing for detection, including radioisotopes, fluorescers, chemiluminescers, particles, ligands for binding to a complementary binding member, which in turn will provide the detectable label, and the like.

The subject compounds may also be used for detecting cells carrying compounds which bind with high affinity to chemotactin, particularly proteins, e.g. receptors for chemotactin and/or its metabolites. Thus, the chemotactin complementary binding member or partner can be readily identified by employing a lysate of cells and including a chemotactin derivative which allows for detection of complex formation between the chemotactin derivative and its binding partner. In this manner, one can identify various leukocytes, particularly phagocytes, which have cellular binding partners to chemotactin and determine agents which result in the up and down regulation of chemotactin binding partner expression. One may also use various chemotactin derivatives as agonists or antagonists to activation of the leukocytes. These compounds may then be used in vitro to screen other compounds, including natural ligands, and derivatives of the natural ligands for their ability to compete in binding to the chemotactin binding partner. In this manner, compounds can be found which will inhibit the chemoattraction of chemotactin for phagocytic leukocytes.

Screening assays for active compounds can be carried out fairly simply by using either purified binding partner or cells which produce the binding partner. In either event, one may have the binding partner or cells bound to a surface, where the binding partner and cells are mobilized under the conditions of the assay. By adding a labeled chemotactin or derivative thereof at a known concentration with the candidate compound, incubating the mixture for sufficient time for the chemotactin derivative and candidate compound to bind, followed by washing to remove any non-specifically bound compound, one can determine the amount of labeled chemotactin derivative bound to the binding partner or cells in the presence and absence of the candidate compound. The lower the amount of chemotactin derivative bound to the binding partner or cells, the greater the affinity of the candidate compound.

One may then use the candidate compound in a conventional chemoattractant assay, where the medium comprising the candidate compound, by itself or in combination with diethyl phthalate, is separated from the medium comprising the cells, particularly phagocytic cells, by a membrane through which the cells can diffuse. The mixture is incubated to allow sufficient time for the cells to travel through the membrane into the compartment with the candidate compound. By determining the number of cells which are present in the compartment containing the candidate compound or the same compartment in the absence of the candidate compound, as compared to the results using known amounts of diethyl phthalate, one can evaluate the activity of the candidate compound as a chemoattractant.

Chemotactin may be used for developing antibodies for use in assays for the detection of chemotactin and its metabolites. In this way, immunoassays may be carried out for the detection of chemotactin. In addition, the antibodies may be used therapeutically to inhibit the effects of chemotactin, by being administered to a patient suffering from inflammation as a result of chemotactin being present in the bloodstream. The amount of antibody employed will depend upon the nature of the antibody, it's affinity for chemotactin, the potential for immune response from the host, and the like. Generally, immunoglobulins are administered at a dosage of about 0.1 μg/L to about 0.5 g/L. Alternatively, one may use compounds which are antagonists to chemotactin, whereby the binding of the antagonist inhibits binding of chemotactin and the homing of leukocytes to the chemotactin site.

In many instances, one may wish to attract phagocytic cells to a particular site, frequently a site where tissue is involved, in vitro or in vivo. For example, one may wish to enhance the inflammatory process. This is particularly true in the case of tumors or other proliferative lesions. In these instances, by introducing chemotactin or agonists, one can enhance the inflammatory response at the site of a lesion, resulting in cytolysis of the cells. Various techniques exist for providing localized concentrations of agents in the treatment of lesions. See, for example, U.S. Pat. No. 4,619,913; Re. 33,375. The amount of chemotactin would vary depending upon whether the natural product is being used or a derivative having a different affinity from the natural product. Generally, the amount of chemotactin would be in the range of about 0.1 μg/kg to 1 mg/kg. Besides the collagen/fibrinogen formulation indicated in the aforementioned patent, other formulations may be employed, using various physiologically acceptable carriers, e.g. water, ethanol, PBS, vegetable oils, and the like. Normally, administration will be localized, rather than systemic.

The availability of a small organic molecule which can be readily detected allows for improved methods for the analysis of the inflammatory process. Since one can readily detect chemotactin, one can also readily identify and isolate cells to which chemotactin is bound to its binding partner. Various techniques are available for distinguishing processes in cells which are responding to chemotactin and cells which do not respond to chemotactin or have not been exposed to chemotactin. In this way, one can prepare cDNA libraries from the different types of cells and use a subtraction library to identify the genes that are being expressed in the presence and absence of chemotactin. Alternatively, one may use representational differential analysis, see PCT/US937/10722 to identify the different genes.

The following examples are offered by way of illustration and not by way of limitation.

EXPERIMENTAL

A. PURIFICATION OF CHEMOTACTIN FROM H. PYLORI SUPERNATANTS

1. Structure of chemotactin.

H. pylori produces diethyl phthalate ("DEP") which causes monocyte chemotaxis. We have termed this novel bacterial factor "chemotactin".

2. Purification of H. pylori chemotactic factor.

Supernatants of H. pylori (ATCC strain 43579 and isolated from a gastric biopsy of a patient with chronic gastritis) were filtered, concentrated, purified by gel permeation chromatography and reverse phase HPLC. Chemotactic activity was measured for each fraction during the purification step and active fractions pooled for the next step of purification. Monocyte chemotaxis was performed in triplicate by placing 50μl of $10^6$ monocytes/ml (obtained from healthy donors) in the upper compartment and 27 μl of test solution in lower compartment. Monocytes that migrated completely through the filter separating the chambers were counted. PBS was used as control. Results were compared to FMLP used as a standard for chemotactic activity. The final step of purification was by reverse phase HPLC on a C-18 column (Vydac, C-18). The column was equilibrated in 0.1% trifluoroacetate, the sample loaded, then the sample was eluted with a gradients of 0–25%/5 min and 25–40%/60 min acetonitrile. The absorbance at 220 nm and chemotactic activity were monitored.

B. CHEMICAL CHARACTERIZATION OF CHEMOTACTIN PURIFIED FROM H. PYLORI SUPERNATANTS

1. Nuclear magnetic resonance (NMR).

The sample was prepared for NMR by reverse phase HPLC of the purified sample on a C-18 column equilibrated in deuterated water containing 0.1M trifluoroacetate and eluted with buffers containing deuterated water and acetonitrile. The sample was then extracted into $CD_3CN$. Residual signals at 1.94 ppm comes from $CH_3CN$, at 2.50 ppm from HOD, and at 5.23 from protonated methylene chloride. Three major signals centered at 7.58 (two quartets), 4.24 (quartet), and 1.28 (triplet) are consistent with the proposed structure of the chemotactic factor. The relative ratio of integrals for these four signals is 4:4:6:3 respectively. The symmetric set of aromatic signals at 7.52 and 7.63 ppm are consistent with an R.R' ortho substituted aromatic ring. The integrated area of four protons agrees with this conclusion. The signals at 4.24 and 1.28 are spin coupled to each other and have the chemical shifts appropriate for ethoxy group. The integrated areas would indicate that two of these groups are present. Synthetic DEP had the same signals slightly shifted (because it was in a different solvent). Addition of DEP to chemotactic factor showed exactly the same signal. The identity of DEP and chemotactic factor is shown by the presence of the same signals when the two were added together.

2. Analysis of samples by combined gas chromatography-mass spectrometry (GC/MS).

Aliquots of HPLC purified chemotactic factor and standards (estimated concentrations 1–100 ng/μl, 1–4 μl) were loaded onto a solvent-free GC injector connected to a bonded-phase medium polarity fused silica capillary column using helium as the carrier gas. The end of the column was inserted directly into the ion source of a modified HP 5985B GC/MS instrument. The injector port and transfer line were maintained at 250° C. and the GC oven was held at 80° C. for 1 minute following injection, and then increased linearly at 10° C./min to a plateau of 300° C. The mass spectrometer was operated in the EI mode with a high energy dynode detector set at -5 KV, and the ion source was held at 200° C. with an ion current of 300 μA at 70 eV. The GC/MS of chemotactic factor and synthetic DEP are summarized in Table 1.

TABLE 1

Comparison of chemotactin and synthetic DEP by GC/MS

|  | Chemotactin | Synthetic DEP |
| --- | --- | --- |
| GC Retention time (run 1) | 6.05 min | 6.12 min |
| GC Retention time (run 2) | 5.98 min | 5.95 min |
| Parent ion mass* | 222 daltons | 222 daltons |
| (Relative Abundance) | (2.0%) | (2.1%) |
| Fragment ion 1 mass* | 149 daltons | 149 daltons |

TABLE 1-continued

Comparison of chemotactin
and synthetic DEP by GC/MS

|  | Chemotactin | Synthetic DEP |
|---|---|---|
| (Relative Abundance) | (100%) | (100%) |
| Fragment ion 2 mass* | 177 daltons | 177 daltons |
| (Relative Abundance) | (21.1%) | (24.4%) |

*Masses and relative abundance values are the average of run 1 and run 2.

The precise GC retention times, the identity of parent and fragment masses, and the similarity of the relative abundance strongly indicate that the natural chemotactic factor, chemotactin, and synthetic DEP have the same structure.

3. Co-chromatography of chemotactic factor and DEP.

Chemotactic factor was chromatographed by gradient reverse phase HPLC. The elution gradient was 25–40% acetonitrile (containing 0.1% trifluoroacetate over 60 min. Next synthetic DEP was chromatographed on the same column in an amount chosen to duplicate the height of chemotactin. The retention times of chemotactin was 36.4 min and synthetic DEP 36.9 min. Finally half of the chemotactin pool and half of the DEP pool were mixed, diluted with three volumes of 0.1% trifluoroacetate, and the mixture chromatographed in the same way. The sharpness of the peak, the height of the peak, and the ratio of 220/280 all indicate that the two were the same compound.

C. CHEMOTACTIN IS THE MOST ABUNDANT CHEMOATTRACTANT IN SUPERNATANTS OF H. PYLORI AND ACTUALLY IS PRODUCED BY THE BACTERIA.

1. There is much more chemotactic activity associated with chemotactin than FMLP.

A sensitive radioimmunoassay for f-Met-Leu-Phe (FMLP) was used to measure the peptide in HPLC fractions of the supernatant from H. pylori. FMLP was easily detected by the radioimmunoassay, but not by the chemotactic assay. The eluent from a reverse phase HPLC of G-50 purified chemotactin was measured for absorbance at 220 nm, FMLP immunoreactivity and chemotactic activity. The predominate peak eluted at 31.6 min and contained the chemotactic activity (chemotactin). The FMLP immunoreactivity was not associated with an absorbance peak. It is proposed that chemotactin is a more likely candidate for expressing chemotactic activity than FMLP because of its abundance and its potential for crossing membranes. The increased potential for crossing membranes comes from the small lipophilic nature of chemotactic.

2. DEP is produced by H. pylori and not another source.

Phthalate esters are common plasticizers that could be found in the plasticware used to grow H. pylori or to process its supernatants. All the manufacturers of plasticware used in these experiments were contacted and all have stated that no phthalate derivatives are used in their products. However, it was felt that this needed verification in our own laboratory. Two control incubations with the same lot of plasticware, the same volume of buffers, and the same incubation times were done. The supernatants from H. pylori and control incubations were concentrated and prepared for HPLC in the same way. The absorbance profiles for the H. pylori and control supernatants were obtained. These data confirm the plasticware manufacturers statement that DEP is not coming from plasticizers.

D. ACTIONS OF CHEMOTACTIN.

The availability of synthetic diethylphthalate has made it possible to do several functional tests.

1. Synthetic DEP causes monocyte chemotaxis.

To confirm the functional identity of chemotactin and DEP, synthetic DEP was added in increasing amounts to the standard chemotaxis assay for monocytes, described above. The number of monocytes chemotaxing to various doses of DEP from 1.25 to 5µM peaked at 1.4µM and diminished to almost control level at 5µM.

2. DEP stimulates intracellular calcium in neutrophils.

All classical chemotactic factors are known to stimulate calcium mobilization and appear to couple to phosinositide-specific phospholipase (Murphy, Annu. Rev. Immunol./ 1994, 12:593–633), suggesting receptor mediated events. We have determined that DEP stimulates calcium release strongly suggesting its actions are receptor mediated. Several concentrations of DEP (1–10µM) were tested; the optimal concentration was 3.3µM.

4. DEP causes inflammation when infected into rat gastric submucosa.

We injected DEP into the submucosa of rat stomach and observed moderate inflammation. We have not had time to optimize the injection protocol, but believe the data is indicative of inflammation caused by DEP.

Doses of DEP (1–10 mM) were injected submucosally (10µl) into the stomach in anaesthetized rats (inactin 90 mg/kg, ip). Sections of DEP-injected stomach with gastric glands and muscularis mucosae were taken. Submucosa demonstrated increased inflammation with swollen myofibrils and moderate increase in inflammatory cells. Fields taken were representative of areas two high power fields from the injection site.

E. CHEMOTACTIN IS DETECTED IN GASTRIC JUICE OF INDIVIDUALS INFECTED WITH H. PYLORI

1. DEP is detected in gastric juice of individuals infected with H. pylori.

Gastric juice from an individual infected by H. pylori was concentrated by solid phase SepPak chromatography. The eluate was diluted in 0.1% trifluoroacetate then chromatographed. The HPLC elution profile of one-half the concentrated gastric juice from an individual infected with H. pylori indicated DEP as the chemoattractant.

It is evident from the above results, that chemotactin can be used as a chemoattractant for phagocytic cells for a variety of purposes. Chemotactin can be used for screening other drugs for their activity as agonists or antagonists-for chemotactin in binding to the chemotactin cellular binding partner. In addition, chemotactin can be used in elucidating the processes associated with the inflammatory process, identifying the cellular binding partner, and investigating the intracellular processes involved with the attraction of the phagocytic cells and their activation. In addition, chemotactin and its metabolites may be used for monitoring the course of infection by H. pylori and other organisms which secrete chemotactin.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for aiding in the diagnosis or following the course of infection by *H. pylori* in a mammalian host, said method comprising:

assaying a physiological sample of said mammalian host in which the secretory product of *H. pylori*, diethyl phthalate, or its metabolites is present during said infection for at least one of said diethyl phthalate;

wherein the presence of at least one of diethyl phthalate and its metabolic products is related to the presence and course of said infection.

2. A method according to claim 1, wherein said physiological sample is urine.

3. A method according to claim 1, wherein said physiological sample is blood.

4. A method according to claim 1, wherein said physiological sample is tissue.

5. A method according to claim 1, wherein said assaying is by chromatography.

6. A method according to claim 5, wherein said chromatography is gas chromatography.

7. A method according to claim 1, wherein said assaying is by an immunoassay.

* * * * *